(12) United States Patent
Santore et al.

(10) Patent No.: US 8,382,858 B2
(45) Date of Patent: Feb. 26, 2013

(54) NANOPARTICLE-TEXTURED SURFACES AND RELATED METHODS FOR SELECTIVE ADHESION, SENSING AND SEPARATION

(75) Inventors: Maria M. Santore, Sunderland, MA (US); Jung Zhang, Neenah, WI (US); Vincent Rotello, Amherst, MA (US)

(73) Assignee: University of Massachusetts, Boston, MA (US)

( * ) Notice: Subject to any disclaimer, the term of this patent is extended or adjusted under 35 U.S.C. 154(b) by 738 days.

(21) Appl. No.: 12/491,851

(22) Filed: Jun. 25, 2009

(65) Prior Publication Data
US 2010/0009379 A1    Jan. 14, 2010

Related U.S. Application Data

(60) Provisional application No. 61/075,525, filed on Jun. 25, 2008.

(51) Int. Cl.
| | |
|---|---|
| *B01D 57/00* | (2006.01) |
| *B82Y 30/00* | (2011.01) |
| *B82Y 5/00* | (2011.01) |
| *B82Y 99/00* | (2011.01) |
| *B81C 99/00* | (2010.01) |

(52) U.S. Cl. ....... 23/293 R; 73/863.21; 95/57; 204/164; 209/127.1; 209/132; 210/767; 423/658.5; 435/7.1; 436/177; 977/902

(58) Field of Classification Search ............... 23/293, 23/293 R; 73/863.21; 95/57; 204/164, 554; 209/127.1, 132–133, 155; 210/748.01, 767; 423/658.5; 435/243, 283.1; 436/177; 977/902
See application file for complete search history.

(56) References Cited

U.S. PATENT DOCUMENTS 3,298,617 A * 1/1967 Engel et al. ............... 241/20
6,143,247 A * 11/2000 Sheppard et al. ......... 436/177 X
6,800,498 B2 * 10/2004 Bright et al. .............. 438/21
(Continued)

FOREIGN PATENT DOCUMENTS

EP        1593745 A1 * 11/2005
WO   WO 2004022338 A2 * 3/2004
(Continued)

OTHER PUBLICATIONS

Fu, Zengli et al., "Poly(ethylene oxide) adsorption onto chemically etched silicates by Brewster angle reflectivity", Colloids and Surfaces A: Physicochemical and Engineering Aspects, vol. 135, (1998), pp. 63-75.

(Continued)

*Primary Examiner* — Thomas P Noland
(74) *Attorney, Agent, or Firm* — Cantor Colburn LLP

(57) ABSTRACT

Textured heterogeneous surfaces and related articles as can be used in conjunction with methods for selective sensing and/or separation. When used for selective particle separation such a system can comprise a heterogeneous surface comprising a surface member and a plurality of components extending therefrom, such components spaced about and having a surface density, with heterogeneity comprising different interactions of the surface member and of the extended components with a particle exposed thereto. Various surface heterogeneities and different interactions can be utilized. However, in certain embodiments, competing electrostatic interactions, or a combination of electrostatic and non-electrostatic interactions, with a particle can be utilized. Such a system can utilize a surface member having a charge difference with respect to the components extending therefrom.

14 Claims, 7 Drawing Sheets

U.S. PATENT DOCUMENTS

| | | | |
|---|---|---|---|
| 7,057,704 B2 * | 6/2006 | Seul et al. | 355/53 |
| 8,117,902 B2 * | 2/2012 | Santore et al. | 73/61.71 |
| 2005/0074478 A1 * | 4/2005 | Ofstead et al. | 424/423 |
| 2005/0118338 A1 * | 6/2005 | Stebe et al. | 427/331 |
| 2006/0167136 A1 * | 7/2006 | Kaneko et al. | 523/160 |
| 2006/0183223 A1 * | 8/2006 | King et al. | 435/372 |
| 2006/0246512 A1 * | 11/2006 | Ezoe et al. | 435/7.1 |
| 2007/0111198 A1 | 5/2007 | Santore | |
| 2007/0264481 A1 * | 11/2007 | DeSimone et al. | 428/220 |
| 2009/0124016 A1 * | 5/2009 | Santore et al. | 436/86 |
| 2010/0021985 A1 * | 1/2010 | Mason | 435/174 |
| 2012/0144904 A1 * | 6/2012 | Santore et al. | 73/61.71 |

FOREIGN PATENT DOCUMENTS

| | | | |
|---|---|---|---|
| WO | WO 2005060668 A2 * | 7/2005 | |
| WO | 2007014267 A2 | 2/2007 | |
| WO | WO 2007024323 A2 * | 3/2007 | |
| WO | WO 2012020402 A2 * | 2/2012 | |

OTHER PUBLICATIONS

Santore, M., et al., "Beyond Molecular Recognition: Using a Repulsive Field to Tune Interfacial Valency and Binding Specificity between Adhesive Surfaces", Langmuir, vol. 25, No. 1, 2009, pp. 84-96.

Shibata, C. et al., "TIRF of Salt adn Surface Effects on Protein Adsorption", Journal of Colloid and Interface Science, vol. 148, No. 2, Feb. 1992, pp. 485-507.

Shin, Yongwoo et al., "The Relationship between Polymer/Substrate Charge Density and Charge Overcompensation by Adsorbed Polyelectrolyte Layers", Journal of Colloid and Interface Science, vol. 247, pp. 220-230, (2002).

Sirvastava, Sudhanshu et al, "Intergrated Magnetic Bionanocomposites through Nanoparticle-Mediated Assembly of Ferritin", J. AM. Chem. Soc., 2007, vol. 129, pp. 11776-11780.

* cited by examiner

NANOPARTICLE-TEXTURED SURFACES AND RELATED METHODS FOR SELECTIVE ADHESION, SENSING AND SEPARATION

This application claims priority benefit from application Ser. No. 61/075,525 filed Jun. 25, 2008, the entirety of which is incorporated herein by reference.

The United States Government has certain rights to this invention pursuant to Grant No. CTS-0428455 from the National Science Foundation to the University of Massachusetts.

BACKGROUND OF THE INVENTION

Dynamic particle capture and adhesion have long been recognized to be important in technological applications ranging from aerosol handling to tribology. This significance now extends into the biological arena. For instance, flowing cells and bacteria are captured on surfaces when neutrophils roll on injury-activated endothelium, during cancer metastasis, and upon initiation of viral and bacterial infection. These behaviors have been reproduced ex-vivo with both cells and rigid round particles functionalized with adhesion proteins to demonstrate underlying principles. Sophisticated biomaterials that achieve similar dynamic and selective control of cells are, therefore, logical candidates for the next generation of diagnostic devices and systems for the refinement of cell suspensions for tissue engineering.

Currently, most research on cell-biomaterial adhesion focuses on the development of materials that bind cells via relatively dense receptor placement on a surface (or tethered from the surface), or relatively concentrated distributions of receptor-bearing nanoparticles. In quiescent conditions, there is an optimal receptor loading for cell proliferation or differentiation: Multiple contacts between the cell and receptors on biomaterials stimulate the formation of an oriented actin network within each cell. Likewise, multiple interaction sites between cells comprise the mechanism for infection, immune response, fertilization, and differentiation of cells. Indeed, Nature seems to have good reason to rely on many weak interactions rather than a few strong ones for cell adhesion and signaling. At the opposite extreme, however, there is technological value to biomaterial-cell interactions generated by one or a few strong contacts. With reports of a receptor threshold for communication between cells, materials that capture cells with a limited number of contacts may be able to do so without the cell's knowledge. That is, limiting the numbers of contacts may facilitate cell manipulation without signaling. Likewise, surfaces which trap cells and particles with just a few or even a single contact can also provide highly sensitive detecting and sensing elements.

SUMMARY OF THE INVENTION

In light of the foregoing, it is an object of the present invention to provide selective separation and sensing compositions and/or articles and methods for the use and/or assembly, thereby overcoming various deficiencies and shortcomings of the prior art, including those outlined above. It would be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide heterogeneous surface compositions, relative amounts of components A and B, surface lengthscales for distribution of A on B, lengthscale for the size and/or height of A domains and/or chemical nature of A and B, for selective electrostatic, non-electrostatic or concurrent electrostatic/non-electrostatic interaction of particles or analytes exposed thereto, such heterogeneity as can be considered in terms of such selectivity at least in part related to particle/analyte size, and/or local curvature.

It can be another object of the present invention to provide such a composition, surface and/or related method to selectively distinguish particles/analytes in a size range from less than about 50 nanometers to greater than about 10 microns, without limitation as to the chemical characteristics of any such particle/analyte.

It can be another object of the present invention to provide any such composition, surface, system and/or related method using spatial dimension, three-dimensional spatial and/or surface configuration and/or density of corresponding surface components to effect or control selective separation or detection.

It can be another object of this invention to provide such a surface randomly configured with the nanoscale features, so as to avoid costly patterning technologies of the prior art.

It can be another object of the present invention to provide a nanodimensioned, heterogeneous textured surface, for use with a related system or method, robust to pH, temperature and/or other environmental factors, and which selectively interacts with target particles or analytes over those outside a predetermined size range or physical/chemical profile characteristic.

It can be another object of this invention to provide such selective interaction without opposite surface/surface component charge required.

It can be another object of the present invention to provide a heterogeneous surface, system or related method, selectively and/or differentially interactive with a range of particles/analytes, each with its own recognition pattern, in lieu of a specific sensor analyte physical-chemical interaction for each particle.

Other objects, features, benefits and advantages of the present invention will be apparent from this summary and the following descriptions of certain embodiments, and will be readily apparent to those skilled in the art having knowledge of various separation/sensing techniques. Such objects, features, benefits and advantages will be apparent from the above as taken into conjunction with the accompanying examples, data, figures and all reasonable inferences to be drawn therefrom, alone or with consideration of the references incorporated herein.

In part, this invention can comprise a method for particle sensing or separation and/or of using a spatial surface configuration for selective particle interaction. Such a method can comprise providing a heterogeneous surface comprising a surface member and a plurality of nanodimensioned components coupled thereto and extending therefrom, such components spaced about said surface and having a density or an average surface density thereon, the heterogeneity comprising different interactions of the surface member and the spaced/extended components with a particle or analyte exposed thereto; exposing a particle or analyte or a mixture thereof to the heterogeneous surface; and sensing different interactions of the particle/analyte, results of such an interaction and/or a combination thereof, or separating a particle mixture with such a heterogeneous surface, selective for such a particle/analyte.

While various interactions, e.g., physical and/or chemical, can be utilized in conjunction with this method, in certain embodiments, the heterogeneity on the surface member can comprise one or more of a range of electrostatic and/or non-electrostatic interactions with a particle or analyte (optionally, of a net charge or comprising another physical or chemical characteristic), whereby the surface member and the extended components thereon can provide variation in surface electrostatic charge and/or other non-electrostatic character (e.g., without limitation, hydrophobicity, van der Waals interactions, hydrogen-bonding capability, etc.). In particular, the extended components can, themselves, have a surface charge density or number, or comprise a variation in surface charge and/or non-electrostatic character, at least partially sufficient for selective particle interaction; and, with surface charge variation, the ionic strength of a medium/solution comprising an exposed particle can be further varied, as determined, to alter or modify selectivity. Regardless, such surface components can also comprise a cross-sectional dimension (e.g., up to about 20 nm or up to about 50 nm) so as to provide such a protrusion from or extension beyond a surface member and an average spatial density at least partially sufficient for selective particle interaction. Such dimension, density and/or ionic strength can be varied as may be required for enhanced selectivity of a specific particle/analyte. Accordingly, spatial density, component charge and/or charge density, component dimension and/or spatial density can be utilized, modified and/or altered for selective interaction with a first particle of a first dimension, such selectivity over a second particle with a second, different radial dimension and/or localized surface radius of curvature. Particle separation and subsequent displacement or collection can provide such a surface for subsequent or repetitious exposure, sensing and/or separation.

Without limitation, particle/analyte sensing can comprise a result of interaction with such a heterogeneous surface, such as a rate of adhesion to a heterogeneous surface and one or more other interactive signatures including but not limited to rolling, skipping and arrest, such interactions as would be understood by those skilled in the art. Accordingly, sensing can comprise one or more signatures or a sequence of signatures for a specific particle/analyte interaction, whereby such a method can be used for selective sensing upon exposure of a particle mixture to such a heterogeneous surface. Removal of adhered/interacted particles permits use of the surface for subsequent exposure, sensing and/or separation.

In part, this invention can also be directed to a system for selective particle sensing or separation. Such a system can comprise a heterogeneous surface comprising a surface member and a plurality of components extending therefrom, such components spaced about and having a surface density, with heterogeneity comprising different interactions of the surface member and of the extended components with a particle/analyte exposed thereto. As discussed elsewhere herein, various surface heterogeneities and different interactions can be utilized; however, in certain embodiments, competing electrostatic interactions, or a combination of electrostatic and non-electrostatic interactions, with a particle can be utilized. Without limitation, such a system can utilize a surface member having a charge difference with respect to components extending therefrom.

In certain embodiments, a surface member can have a net negative charge, and a extended component, as can comprise a functionalized nanoparticulate composition, can comprise a net positive charge. Such an embodiment is available through deposition of one or more of several synthetically or commercially available nanocomposites onto a silica surface at levels below those corresponding to surface saturation (e.g., without limitation, up to about 50% of saturation). Component spacing can be optimized to provide selective interaction of such a heterogeneous surface with a specific particle/analyte. As but one departure from the prior art, under conditions of the sort described herein, the minimum interaction for adhesion or capture can be a single extended component for a particular analyte. In certain non-limiting embodiments, such an extended nanoparticulate component can comprise a metal core (e.g., without limitation, a precious metal such as gold) with a shell component thereabout. Such components can be of nanometer dimension to sense micron-dimensioned particles. Without limitation, component dimension and extension from a surface member can exceed the Debye length of a medium comprising an exposed particle/analyte, such a distance at least partially sufficient to provide a heterogeneous energy landscape with respect to an exposed particle/analyte at a given ionic strength. Regardless, spacing or density can be varied, separately or in conjunction with the size and/or charge density of the extended components. Accordingly, as described more fully below, such a system can be designed and used to selectively sense or separate particles of a given dimension or chemical/physical characteristic.

In part, this invention can also be directed to a method for determining particle signature. Such a method can comprise providing a heterogeneous surface comprising a surface member and a plurality of extended components thereon, such components spaced about and having an average density on the surface member, with the surface heterogeneity comprising different interactions of the surface member and extended components with an exposed analyte/particle, such a heterogeneous surface selectively interactive therewith; exposing one or more known particles to the heterogeneous surface; sensing interactions of the known particles with the heterogeneous surface; and determining one or more signature interactions, in recognition of each known particle. Such signature(s), once determined, can be used for purposes of comparison with a signature of an unknown particle/surface interaction to identify the unknown particle.

As mentioned above and discussed more fully below, surface heterogeneity can give rise to various different or competitive surface interactions (e.g., without limitation, electrostatic vs. van der Waals interactions) with an exposed particle. Likewise, in certain embodiments, a surface member and components extending therefrom can comprise domains of charge (or, e.g., chemical) variation for different electrostatic and/or non-electrostatic interaction with a particle having a net charge or physical-chemical affinity. Charge density, surface spacing, spatial density and/or component extension from the surface member can be varied for selective or optimal interaction of such a heterogeneous surface with a particle/analyte of a given dimension or curvature. Such signatures, e.g., results of such interactions, can comprise adhesion, arrest, rolling, skipping and/or other interactive signatures recognized by those skilled in the art, whereby an interactive pattern can ascertained, in recognition of the known particle. As such, exposure of a second or unknown particle and comparison with a recognized interactive signature can be used to determine or assess identity of a second/unknown particle.

In part, as can be apparent from the preceding discussion, the present invention can also be directed to an article of manufacture or device, or related system, comprising a heterogeneous surface for selective analyte sensing or separation. Such an article can comprise a surface member and a plurality of spaced components extending therefrom and coupled thereto, such a surface member and spaced components providing a surface heterogeneity selected from different electrostatic interactions, different non-electrostatic interactions and a combination of said interactions, such that the interactions are at least partially sufficient for selective analyte interaction and/or separation. Without limitation to any one theory or mode of operation, such component extension can be of a nanometer dimension about the Debye length of a medium comprising an analyte particle exposed to such a surface. Without limitation, an analyte particle, optionally of a mixture of particles, can be dimensioned from about 30 nm to about 20 µm. As discussed and/or illustrated below, such a component dimension about a Debye length can be less than, greater than or equal thereto, depending on desired effect. Regardless, in certain embodiments, the extended components can be of a density at least partially sufficient for interaction of a single such component or multiple components with a single analyte particle, at a given Debye length. In certain other embodiments, such components can comprise an average spatial density at least partially sufficient for selective particle interaction and/or separation.

Without limitation, in certain embodiments, the spaced components can extend up to about 20 nm or up to about 50 nm from and/or beyond the surface member. In certain such embodiments, the components can comprise a nanoparticulate composition comprising a metal core and a shell component thereabout. Component dimension can comprise the core/shell diameter. In certain such embodiments, a core can comprise a precious metal and a shell can comprise ligands selected from cationic and anionic ligands. Where such compositions comprise cationic ligands, the extended components can comprise a net positive charge. As illustrated below in the context of various non-limiting examples, a heterogeneous energy landscape can be provided with a surface member comprising a net negative charge. Representative embodiments of such an assembly can comprise extended components comprising gold coupled to ligands functionalized with quaternary ammonium salt moieties and a surface member comprising silica.

DETAILED DESCRIPTION OF CERTAIN EMBODIMENTS

Figure 1:
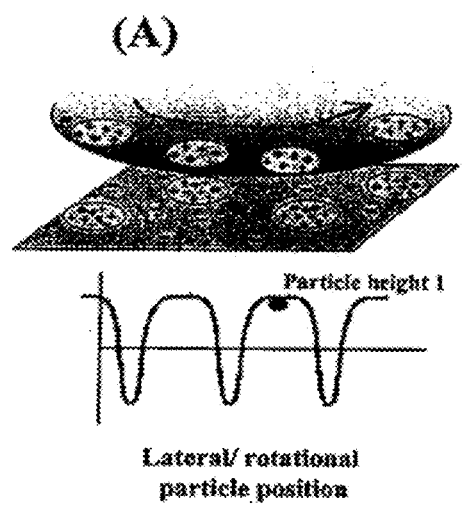
FIGS. 1A-D. Schematic representations illustrating particle surface interactions.
Figure 1:
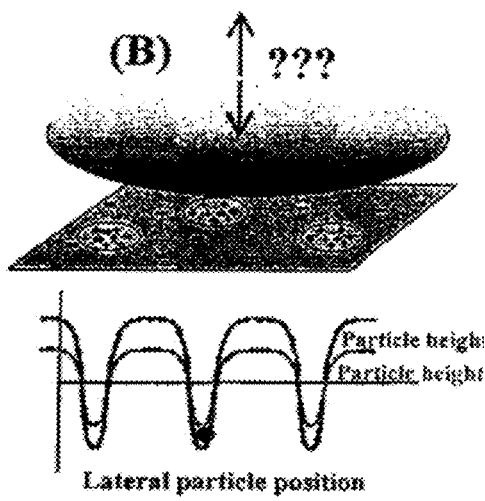
Figure 1:
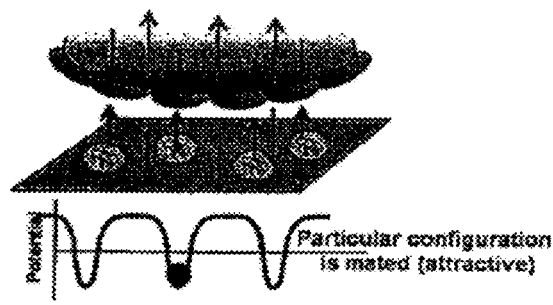
Figure 1:
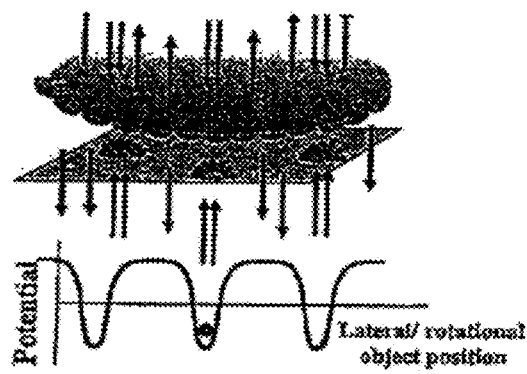

Without limitation to any one theory or mode of operation, various aspects and features relating to certain embodiments of this invention can be considered in conjunction with co-pending application Ser. No. 11/592,454 filed on Nov. 3, 2006, the entirety of which is incorporated herein by reference. In FIG. 1B thereof, a negative micron scale sphere interacts with a negative surface carrying flat patches of multiple positive charges, where the patches are substantially smaller than the sphere. At any position, the sphere experiences both attractions and repulsions at different points on its surface. The sphere is currently in an attractive well, and translation of the sphere over the surface results in a height dependent spatially varying potential. A different sized sphere would experience a different proportion of attractions and repulsions such that the heterogeneous surface will attract some particle sizes better than others. In the experimental scenario of FIG. 1B of the aforementioned co-pending application, a relatively smooth negatively charged particle interacts with an electrostatically heterogeneous surface presenting attractive (positive) domains on an otherwise repulsive (negative) surface, where the domains are small relative to the particle size. Lateral variations in surface charge (the heterogeneous domains) attract or repel the sphere, depending on its position in the x, y, and z directions. Thus the approaching sphere experiences a potential energy landscape. In FIG. 1B, the particle experiences this landscape by translating across the surface. This situation is similar to the more classical pattern recognition situation, in FIG. 1A (of the co-pending application) where, with a pattern on both sides of the interface, attractions and repulsions result from particle translation and rotation. The surface of the micron-scale sphere illustrated in FIG. 1A contains multi charged positive domains. Depending on the size and spacing of the positive domains on the sphere relative to those on the surface, pattern recognition and adhesion, with various dynamic signatures, may or may not be achieved, thus producing selectivity. In the example shown, the size and spacing of the domains on the sphere are similar to those on the heterogeneous planar surface giving rise to the possibility of adhesion. The sphere is currently in a repulsive maximum and translation or rotation will cause the potential to vary. A slight rotation or translation from the current position would move the sphere towards a local minimum, producing adhesion. If the patch distribution on the sphere were out of registry with that on the plane, a more complicated potential with weaker attractions would result. Likewise in FIG. 1C, a similar affect may be observed for a particle with surface roughness of a particular lengthscale, but a relatively uniform charge distribution, in this case negative. Here, the analyte is not a sphere, but an aggregate of smaller primary spheres, carrying only negative charge. In addition to the lengthscale of the overall analyte particle, there is a lengthscale of the small primary spheres making up the aggregate. In this example, the small sphere lengthscale is in registry with the lengthscale implicit in the heterogeneous surface, giving rise to attractions. A different size primary particle in the aggregate would break this registry and reduce attractions and adhesion.

While this invention can be considered to implement such features, it represents a departure from the prior art in that nanodimensioned, immobilized particles extending from or protruding beyond a surface member are used to provide a nano-scale heterogeneous energy landscape. This invention can be demonstrated using the interactions between micron scale silica particles and planar surfaces containing nanoconstruct particles of varied surface density (with the remaining surface area being relatively repulsive towards the particles). Rather than AFM, colloidal probe, or surface forces methods, particle deposition from gently flowing solution was employed to assess the interactions from a practical perspective and to demonstrate pattern recognition-like, selective features of the interactions. Adhesion rates were observed as a function of the nanoparticle component density, and a certain range of surface conditions were found to promote adhesion, much like the concept of interfacial pattern recognition.

With reference to FIG. 1D, the present invention can be considered in the context of nano-scale clusters of defined functionality on a surface, with placement at a controlled lengthscale, whether random or ordered. Nanoparticle functionality need not be that of or mimicking a biomolecule, although surface components of the present invention can be employed in conjunction with biomolecular functionalization. In one respect the heterogeneous surfaces of the present invention differ from the prior art in that nanoparticles, whether or not bio-functionalized, extend beyond or protrude from a surface member. As demonstrated by various non-limiting embodiments, such nanoparticles can be used to provide an energy landscape of localized attractions (e.g., nanoparticle(s) to an analyte) in an otherwise repulsive field (e.g., a surface member). In addition to such electrostatic factors, use of the present nanoconstructs provides a three-dimensional staggering of attractive elements relative to a repulsive background field, and represents a new factor in an overall heterogeneous energy landscape.

With an objective of demonstrating the capture of micron-scale objects with minimal interactions, various non-limiting embodiments of the present invention illustrate a cell-free and biomolecule-free system of localized (e.g., ~10 nm, the size of proteins) attractive surface regions to capture and adhere much larger flowing micron-scale particles—even though the background surface and hydrodynamic fields are substantially repulsive. Such a non-biological approach can quantitatively demonstrate, without commitment to a particular ligand-receptor pair, the physics of particle adhesion in the limit of one binding site per microparticle. Accordingly, the present surface design strategy can be used to recreate features of a cell surface: On cells, attractions occur at distinct points (receptors) while the glycocalyx provides a background field that is repulsive to most biological objects. This invention employs a parallel construction: an electrostatically repulsive background field in which attractive nanoparticle-based adhesive elements are distributed. The results confirm a regime where micron-scale objects, representative of bacteria and biological cells, can be captured and held by single nanoparticle surface constructs.

Various embodiments of this invention, employing cationic nanoparticles as adhesive elements, can be distinguished from particle capture with flat cationic patches. Qualitative differences between the adhesive behavior in the nanoparticle system and that using patches are demonstrated below. Further, such nanoparticles can be used to examine strength of binding by attempting to dislodge adherent microparticles with flow, in the limit where the microparticles are held by a single nanoparticle. As shown, the electrostatic attractions, even for a single 10-nm contact region, can be tuned to be far in excess of accessible hydrodynamic forces, or they can be tuned to be small relative to hydrodynamic forces. The nanoparticle-containing surfaces therefore exhibit highly efficient capture and a tunable means of particle and cell manipulation. Application of these design principles can facilitate extremely sensitive detecting surfaces and surfaces that capture, adhere, and release cells, with minimal biological response. The findings here are also relevant to technologies exploiting mixed flocculation conditions, following advances in heteroflocculation.

Figure 2:
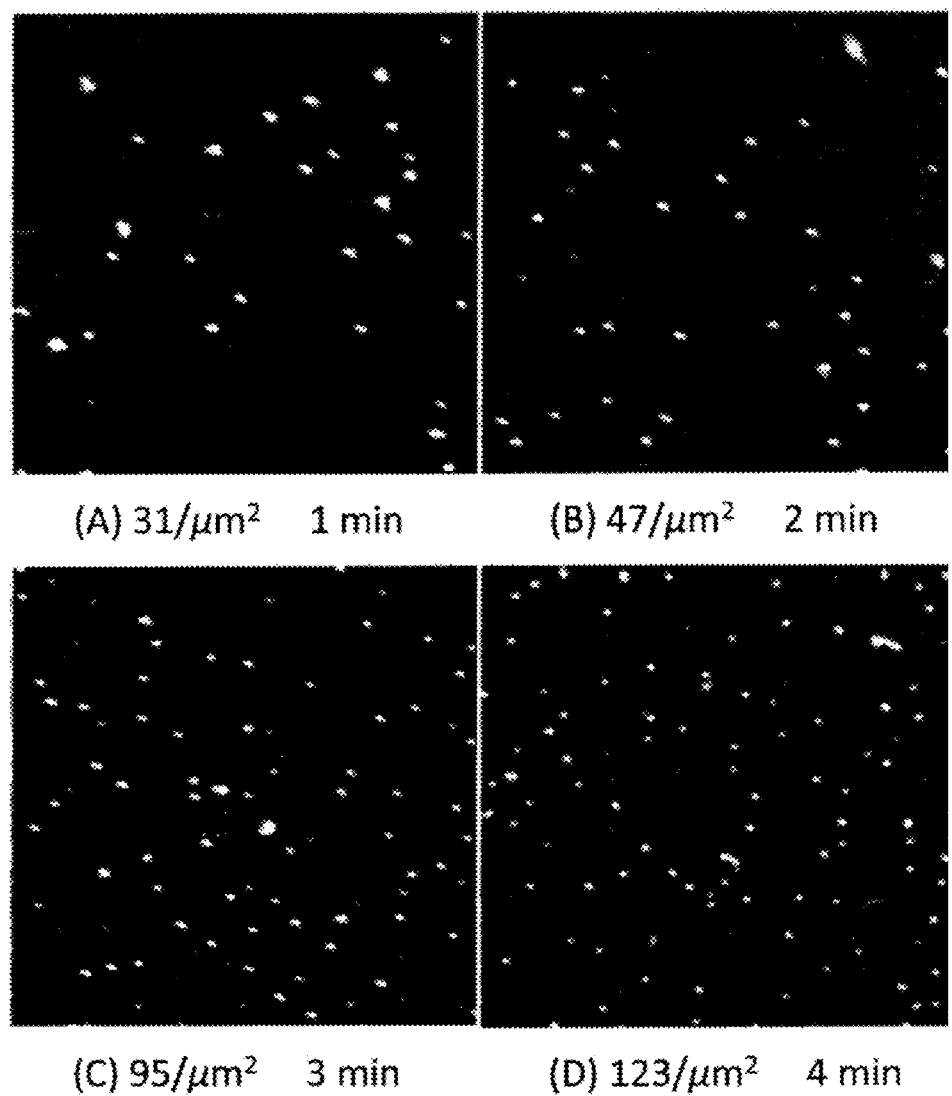
FIG. 2. Representative AFM micrographs, measured dry, of cationic nanoparticles on acid-etched microscope slides.

The micrographs of FIG. 2 provide AFM images illustrating the arrangement of the gold nanoparticles on glass slides, for different exposure times of the slides to the nanoparticle suspension, resulting in different densities of gold nanoparticles thereon. Without limitation, such micrographs demonstrate a range of nanoparticle densities down to 31/um$^2$, and up to 123/um$^2$. (Higher densities are demonstrated in FIGS. 3 and 4, below.) The figure emphasizes the random placement of the particles on the surface and the lack of nanoparticle aggregation on the surface. Of note, the particles in this figure appear larger than the 10-11 nm diameter size of the ligand-covered particles, due to AFM tip convolution effects. The number of particles per unit area, and their arrangement is not affected by tip artifacts. The number of nanoparticles deposited per unit area is proportional to the flow time of the nanoparticle suspension, as a result of the flow cell employed for nanoparticle deposition. Similar deposition could be achieved by immersing objects in a bath of nanoparticles; however, the exposure times leading to different surface densities of nanoparticles would need to be calibrated.

Figure 3:
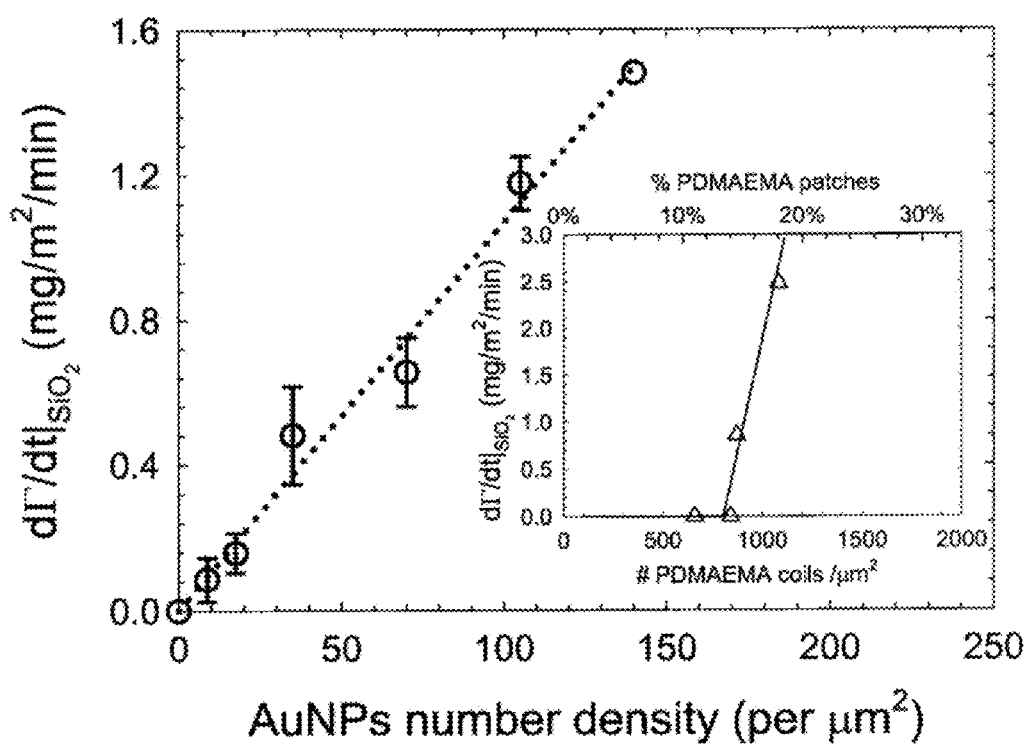
FIGS. 3-4. Capture rates of 1 µm spherical silica particles, dΓ/dt($SiO_2$) from flowing suspensions, in pH 6.1 buffer 0.005M; $\kappa^{-1}$=4.24 nm (FIG. 3) and $\kappa^{-1}$=13.8 nm (FIG. 4).

The dynamic capture of silica microparticles on a series of surfaces containing different densities of cationic nanoparticles is shown in FIG. 3. Here, the microparticle capture rate on these surfaces increases linearly with nanoparticle density on the substrate, starting at the origin. This seemingly straightforward result represents an extreme in the behavior of microparticle capture. The observation that the data intersect the origin suggests that no matter how sparsely the cationic nanoparticles are positioned on the surface, some silica microparticles will eventually be captured. Without any nanoparticles, however, the collecting surface captures no silica microparticles. This means that a silica flat containing only one cationic nanoparticle would eventually capture and hold a silica microparticle. Thus, these cationic gold nanoparticles, when placed on a negative surface, are each capable of capturing and holding a much larger object.

The significance of the intersection with the origin in FIG. 3 is put into perspective by comparison to the ability of a second type of surface (inset) to capture the same 1-micron silica particles: For collecting surfaces that contained 11 nm cationic polymer "patches" that held their positive charge relatively flat to the surface, the rates of 1-micron silica particle capture (at the same pH and ionic strength as in FIG. 3), showed a positive x-intercept near 800 patches/μm$^2$, rather than passing through the origin. Therefore, the collecting surfaces decorated sparsely with cationic patches were completely non-adhesive towards approaching negative microparticles. The observed behavior suggested that the mechanism of microparticle capture involved multiple cationic patches acting on a single silica microsphere.

Data from nanoparticle functionalized surfaces of this invention were collected with a wall shear rate of 20 s$^{-1}$, while the older data in the inset with the cationic patches were at a flow rate of 39 s$^{-1}$. This difference was a result of the different flow cells on the different instruments in the two studies. Since the effects of flow generally produce a wall shear to the ⅓-power scaling of the mass transport-limited particle capture rate, differences between 20 and 39 s$^{-1}$ are small. More importantly, the present functionalized surfaces (data not provided here) show that for wall shear rates of at least up to 100 s$^{-1}$ data like those in FIG. 3 continue to pass through the origin. Therefore, the qualitative differences between particle capture by surfaces functionalized with flat patches and those functionalized with cationic nanoparticles is preserved over a wide variety in flow rates.

The action of the flat cationic patches is believed to mimic the common biological situation where multiple ligand-receptor bonds engage at cell-cell contacts, while the current data in FIG. 3 represent a more extreme behavior. By comparing current and prior data, it can be concluded that the difference between multiple interactions versus a single contact to capture a microparticle can be due to the raised nature of the current cationic nanoparticles. As such, the present invention quantitatively demonstrates how the relative range of attractive and repulsive interactions translates to dynamic adhesion and particle capture.

By way of further comparison, in the adsorbed polymer (flat patch) case, all positive charges are potentially exposed towards the solution but the actual charge after counterion condensation is about 75. In the case of the current raised nanoparticles, the positive charges are spaced over the surface of the sphere, so that counterion condensation is much smaller; however, roughly half of the cationic charge lies between the nanoparticle and the substrate, so that approaching silica microparticles do not feel the attraction from roughly half, about 100, cationic groups. A difference, then, between the collecting surfaces, is that with the nanoparticles, some of the positive charge is extended or positioned beyond the electrostatically repulsive surface field of the silica.

Another point of comparison between the nanoparticle-bearing surfaces of FIGS. 2-3 and other adhesive situations involving 1 μm spheres is that the contact area between the microsphere and nanoparticle-containing surfaces, on the order of 80 nm$^2$, follows from the diameter of the nanoparticle squared. The same microparticle interacting with an electrostatically attractive flat substrate at this ionic strength will have an effective contact area of 13,000 nm$^2$, based on the intersection of the Debye layer around the sphere (4.24 nm in the case of the 0.005 M buffer) with a planar surface. Hence, in the context of the current data, the contact between the microsphere and the collector is localized by the nanoparticles and this, in turn constitutes a means of applying force to an extremely small region of contact.

Figure 4:
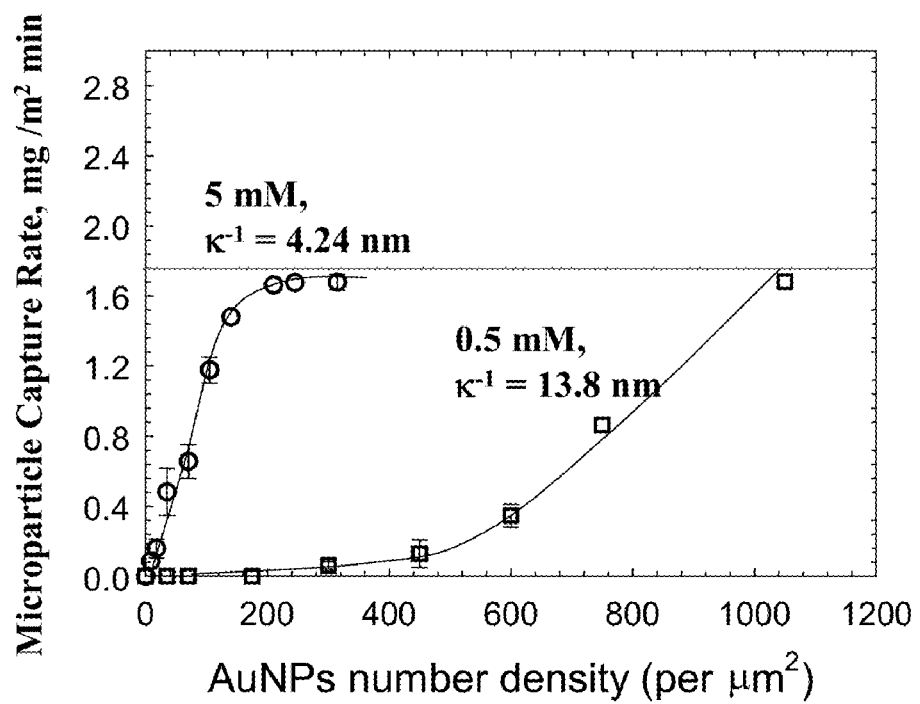

Various other considerations are presented with the data of FIG. 4. As with FIG. 3, the data consisting of circles set has been generated in a pH 6.1 phosphate buffer (KH$_2$PO$_4$) having an ionic strength of 0.005 M, corresponding to a Debye length of 4.24 nm. At low nanoparticle densities on the collecting surface (the left side of the graph), the silica particle adhesion rates (circles) increase with increasing nanoparticle density, while above 200 nanoparticles/dm$^2$, the silica particle capture rate (circles, still) is constant and corresponds to transport-limited particle adhesion. (Transport limited particle adhesion occurs when the silica particle binding events are so favored, and fast, that silica particles reaching the surface stick as quickly as they can diffuse from the bulk solution to the interfacial region.) The particular transport limited silica particle capture rate for this example, 1.7 mg/m$^2$/s, corresponds quantitatively to the predictions of the Leveque equation, which is the established model for slit shear flow cells such as the one used in this example.

As discussed above, a reason why single nanoparticles can capture microspheres (as compared with their flat analogs of adsorbed proteins and polycations) may be that (1) they are densely functionalized with groups that are attractive to a target/analyte and (2) they extend beyond the range of the repulsive field (in the initial example of FIG. 4, the range of the background repulsion is the Debye length, 4.24 nm).

Making the range of the attractions and repulsions more nearly similar is accomplished by a decrease in ionic strength, which increases the Debye length and increases the range of the repulsive background field. Initial studies in an extreme limit of low ionic strength, corresponding to a Debye length of 13.8 nm, showed that over a very large range of cationic nanoparticle densities on the collecting surface, e.g., up to and greater than 200 nanoparticles/um$^2$, 1 micron silica particles do not adhere to the collector. These are the data (squares) on the x-axis of FIG. 4. Ultimately, greater densities of cationic nanoparticles on the collector do capture silica particles from free solution, producing an adhesion threshold. However, the data shown here bracket the two extremes of possibility: From highly exposed and attractive surface elements that easily adhere single microparticles, to attractive surface elements that become hidden in the background repulsive field. For Debye lengths near 13 nanometers, the adhesion threshold and the curvature selectivity of the prior co-pending applications will be recovered. Indeed, both the polycation and fibrinogen-based surface elements established the general trends for the effect of ionic strength on the adhesion threshold, for heterogeneous surfaces whose main surface member repels approaching particles.

Figure 5:
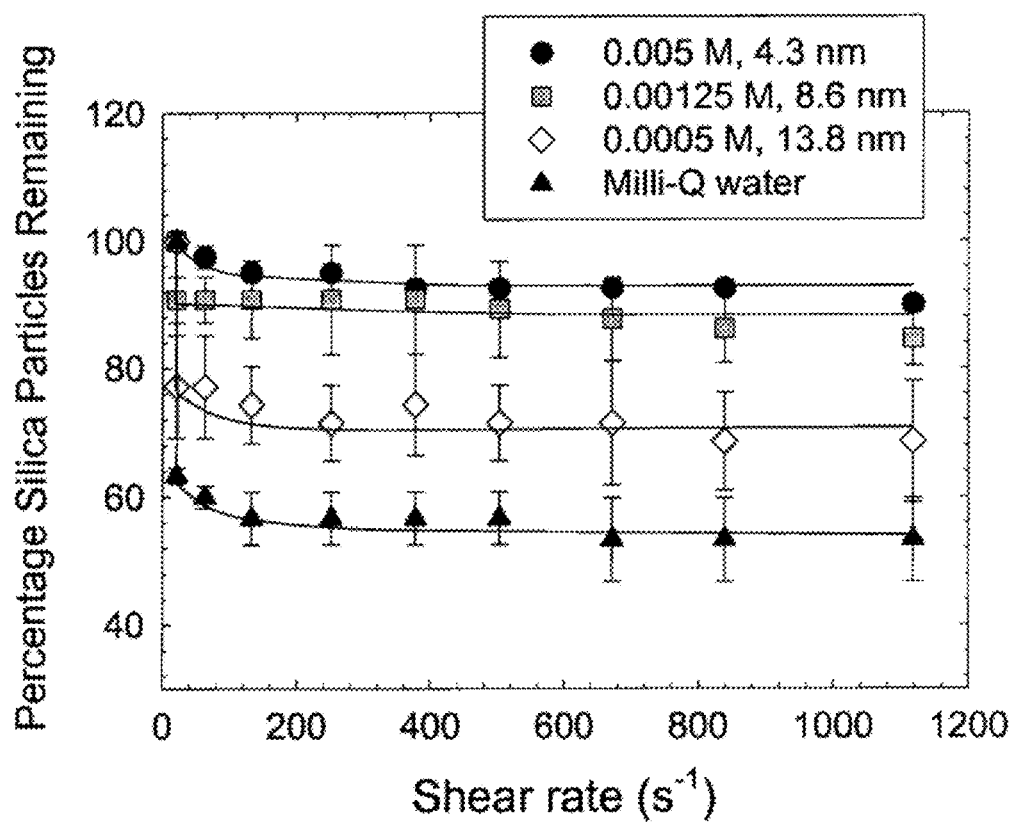
FIG. 5. Fraction of silica particles remaining after adjustment of ionic strength and shear rate to remove adherent silica particles. The silica particles were deposited in 0/005 M pH 6.1 phosphate buffer onto a collecting surface with 9 cationic nanoparticles/µm². All data points are relative to this initial condition for silica adhesion. Curves guide the eye and emphasize that all data sets start with "100%."
Figure 6A:
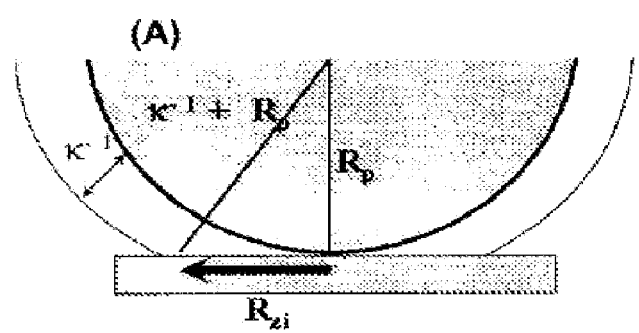
FIGS. 6A-B. Schematic illustrations of a (A) Limited collector, of radius Rzi (zone of influence) area acts on a particle depending on the Debye length, or (B) where $R_{zi}$ can be smaller, when a microparticle rests on a single nanoparticle, making an encounter with a second nanoparticle less influential.
Figure 6B:
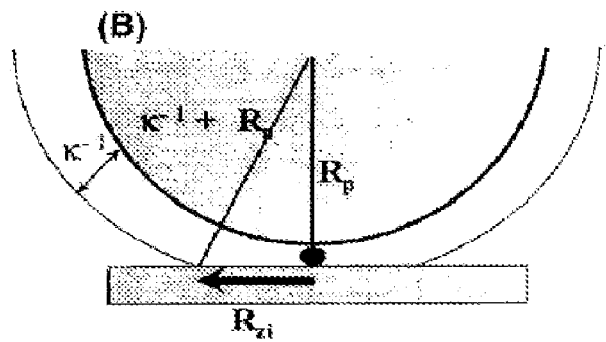

The forces that capture the silica particles in FIGS. 3-4 turn out to be quite strong, and hold the silica particles on the otherwise repulsive silica flat in strong shear. FIG. 5 illustrates this point by examining the behavior of 1 μm silica particles that have already adhered to collecting surfaces and are subsequently challenged by strong shear or different ionic conditions. In FIG. 5, the collecting surfaces contain 9 nanoparticles/μm$^2$, which is in the regime where silica particles are held by single nanoparticles to the collector. (This condition corresponds to the sparsest nanoparticle datum in FIG. 3). The argument for action by single nanoparticles follows from the limited area on the collecting surface that is actually able to interact with a micron-sized sphere, as provided in in FIG. 6A, which is a schematic illustration of a collector having a limited radius of interaction with the approaching particle Rzi (zone of influence), or FIG. 6B, which is a schematic illustration where Rzi can be smaller. The 4.24 nm Debye-length shell around a one-micron diameter sphere intersects a planar surface, subtending a radius of 65 nm. Therefore, only 13377 nm$^2$ (0.013 μm$^2$) of collecting surfaces exerts electrostatic force on a micron-sized silica sphere in contact with the surface. Assuming a random (Poisson) distribution of nanoparticles on the collecting surface, with an average of 9 nanoparticles per μm$^2$, the probability ratio of encountering one versus two nanoparticles in an area of 13377 nm$^2$ is 16.6. Hence there will be more than an order of magnitude more silica particles held by single rather than two nanoparticles. This represents a worst case estimate, as electrostatic repulsions between nanoparticles during the deposition process likely truncate the Poisson distribution of gold nanoparticles. That is, AFM data in FIG. 2 and other similar images reveal negligible occurrences of closely situated nanoparticle pairs on collecting surfaces.

In generating FIG. 5, approximately 30 silica particles were first allowed to be captured from gentle flow (a wall shear rate of 21 s$^{-1}$) and an ionic strength 0.005 M (corresponding to a Debye length κ$^{-1}$=4.24 nm) in the field of view (128 μm×96 μm) of the microscope. This avoids particle-particle interactions and related hydrodynamic effects. Studies were repeated with multiple slides and different regions of each slide were examined. After the silica particles were allowed to adhere, the flow was increased step-wise, ultimately up to a wall shear rate of 1118 s$^{-1}$, corresponding to a force of 9 pN on an immobilized nanoparticle. The experiments were repeated with fresh slides, always depositing the gold nanoparticles from DI water and adhering the silica microspheres at an ionic strength of 0.005 M and a shear rate of 21 s$^{-1}$, but then subsequently adjusting the ionic strength to a new level (to generate an entirely new family of data), and subsequently increasing the flow rate after that. It was observed that particles were released mostly when the ionic strength was reduced, rather than when the shear was increased. This indicates that though the interactions are strong (from the practical perspective) they are also reversible.

As shown in FIG. 5, shear had little impact on silica particle retention at several ionic strengths. For each ionic strength, roughly 5-10 percent of the particles were removed as the shear was increased from 21 to 133 s$^{-1}$. Further increases in shear, up to 1118 s$^{-1}$, did not substantially dislodge particles. The ionic strength was, however, more important than shear, a result of the predominantly electrostatic nature of the interactions. FIG. 5 indicates that increases in the Debye Length above 9 nm caused a substantial fraction of the particles to be released in gentle shear conditions. Debye lengths less than 9 nm had only a small effect on silica particle retention. This is consistent with the 11 nm nanoparticle size.

The insensitivity of particle retention to shear demonstrates that the electrostatic forces are orders of magnitude stronger than the hydrodynamic forces. Further, the sensitivity of particle retention to ionic strength demonstrates the importance of electrostatics relative to van der Waals attractions. As the Debye length is increased, so too follows the range of the electrostatic attractions from the nanoparticles and the electrostatic repulsions from the underlying substrate. As the Debye length approaches the particle diameter, the fact that the nanoparticle attractions protrude from the background repulsive field becomes unimportant: With a greater area of repulsive chemistry relative to a small single nanoparticle, repulsions dominate at large Debye lengths, causing silica microparticles to release. There are, of course, practical experimental limits on the Debye length, for instance from dissolved gasses. Also, as one moves in the direction of large Debye lengths, the buffering capacity of the solution is lost, hence the silica surface potential is not controlled and silica repulsions become compromised. Regardless, as evidenced, component dimension and/or Debye length can be varied to effect desired analyte behavior.

Various embodiments of this invention represent a class of material surfaces that, when exposed to analyte suspensions containing target objects (e.g., organic, inorganic, biological such as bacteria cells and viruses, in the size range from about 30 nm to about 20 um), will selectively adhere the target objects while rejecting non-target objects. The selective adhesion may be permanent binding of the target, but it may also be reversible binding of the target, or adhesion sufficiently loose that when the interface is exposed to flow or other fields that impose forces on the objects, the objects will roll, skip, or slide in ways that distinguish them from non-target objects. Various aspects are illustrated here with planar collecting/sensing surfaces; however, the preparation methods described here can be modified, as would be understood in the art, to accommodate the functionalization of arbitrarily shaped objects, packing materials, fibers, and the like.

EXAMPLES OF THE INVENTION

The following non-limiting examples and data illustrate various aspects and features relating to the methods and/or articles of the present invention. In comparison with the prior art, the present methods and articles provide results and data which are surprising, unexpected and contrary thereto. While the utility of this invention is illustrated through the use of several articles and surface members and spaced/extended components which can be used therewith to sense, detect or separate a representative analyte, it will be understood by those skilled in the art that comparable results are obtainable with various other articles/devices and components/surface members to sense, detect and/or separate various other analytes, as are commensurate with the scope of this invention.

Example 1

The surface system consists of a negative surface (silica) that electrostatically repels negative objects (e.g., monodisperse silica microparticles), but which contains 11-nm nanoparticles that are densely and positively charged. The cationic nanoparticles were built from 7.5 nm gold cores, with a shell of approximately 500 ligands: For instance, about 200 N,N, N-trimethyl(11-mercaptoundecyl)ammonium chloride side chains, and about 300 1-mercaptoundecane chains. This brought the diameter of the nanoparticles up to 11 nm (dry, by TEM), or 15 nm in solution as measured by dynamic light scattering. (Srivastava, S.; Samanta, B.; Jordan, B. J.; Hong, R.; Xiao, Q.; Tuominen, M. T.; Rotello, V. M. *J. Am. Chem. Soc.* 2007, 129, 11776-11780.) Each nanoparticle therefore contained 200 quaternary amines distributed over its otherwise hydrophobic surface ($4\pi r^2 = 380$ nm$^2$) with an average spacing of 1.38 nm. The zeta potentials of these nanoparticles were 20.5±3.3 mV in DI water and 26.6±1.3 in 5 mM pH 6.1 phosphate buffer.

Example 2

Figure 7:
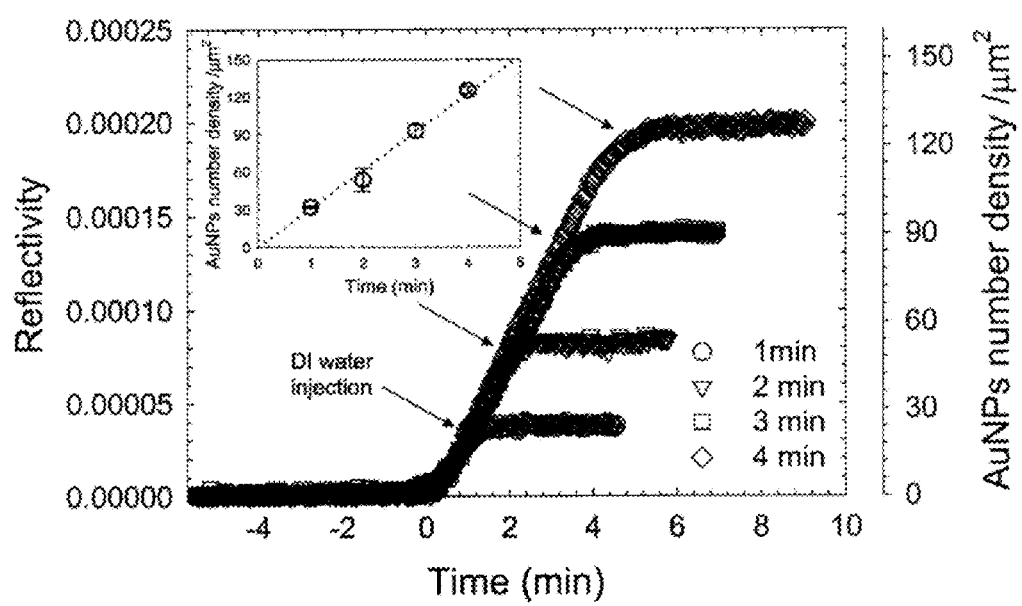
FIG. 7. Representative data for deposition of cationic gold nanoparticles on acid-etched microscope slides, measured by near-Brewster reflectometry. The nanoparticle concentration is 20 ppm in DI water, with a share rate of 10 $s^{-1}$. Arrows indicate reinjection of DI water to stop additional particle deposition. Cationic nanoparticles were then retained in flowing DI water, as indicated by the flat signal after reinjection of DI water. The inset shows average deposition amounts for several runs of different depositions times.

The collecting/sensing surfaces were microscope slides that were acid etched for 15 hours in Piranha solution ($H_2SO_4/H_2O_2$, 3:1 by volume) at 70-80 C, and then rinsed with copious amounts of DI water. To create collecting surfaces, cationic nanoparticles were randomly deposited from dilute aqueous solution (20 ppm in DI water) on the silica surfaces of the microscope slides, using a slit shear flow cell with a known mass transport coefficient. (Fu, Z. G.; Santore, M. M. *Colloid Surface A* 1998, 135, 63-75. Shibata, C. T.; Lenhoff, A. M. *J. Colloid Interface Sci.* 1992, 148, 485-507.) The nanoparticle density could therefore be precisely controlled through the flow time (e.g., about 15 seconds to about 20 minutes, depending on density desired) of the nanoparticle suspension. (Shibata, C. T.; Lenhoff, A. M. *J. Colloid Interface Sci.* 1992, 148, 485-507.) After the desired flow time, DI water was re-injected into the chamber to halt nanoparticle deposition. FIG. 7 presents examples of the nanoparticle deposition curves, measured by near-Brewster optical reflectometry. (Fu, et al., supra.) (The flow rate for this particular series was 10 s$^{-1}$). The bound nanoparticle density is linear in flow time over the range of interest, below saturation of the surface by gold nanoparticles. The deposition rate (30 particles/μm$^2$ min, in this example) is generally proportional to the nanoparticle concentration in solution, and scales as the flow rate to the ⅓ power, as would be expected for mass transport particle deposition.

Example 3

AFM images of the resulting surfaces are shown in FIG. 2, obtained after the surfaces were rinsed and dried. Indeed, the particles per unit area, measured by AFM, quantitatively agree with the mass-transport-limited nanoparticle deposition rates from near-Brewster reflectometry (for particles of a 15 nm hydrodynamic radius), providing confidence that the particle densities (number of nanoparticles per area) in FIG. 2 are representative of much larger surface areas, on the order of millimeters, seen by reflectometry. The ultimate arrangement of the particles on the surface appears random, and tends not to contain closely positioned nanoparticles. These observations are consistent with strong nanoparticle adhesion: There is no evidence for diffusion of the nanoparticles on the surface during the deposition or drying processes. Indeed, the particles exhibit no removal on drying, immersion in organic solvent, moderate pH changes, large changes in ionic strength of solution, light mechanical brushing or sonication in aqueous or organic solvent. While the initial driving force for particle deposition is the electrostatic attraction between the cationic groups on the nanoparticles and the negative silanols on the silica flat, strong van der Waals forces can be considered to hold the particles in place.

Example 4

For the full range of collecting surfaces used in the present microparticle capture experiments, the collecting surfaces were net negative. Indeed, up to about 200 nanoparticles/dm$^2$, the ζ-potentials are experimentally indistinguishable from that of bare silica. (−58 mV at pH 6.1 in 0.005M phosphate buffer ($KH_2PO_4$)). This was determined by examining the electrophoretic mobilities of 1 μm silica particles onto which known amounts of cationic nanoparticles had adsorbed, as described in the literature. (Shin, Y. W.; Roberts, J. E.; Santore, M. M. *J. Colloid Interface Sci.* 2002, 247, 220-230.)

Example 5

Studies of microparticle capture and resistance to shear forces were conducted in a flow chamber of similar design to that for nanoparticle deposition, except now with a clear back panel to facilitate illumination from the rear. This chamber was placed on a home built lateral microscope where a 20× objective focused the image of the collecting surface onto a video camera. A suspension of monodisperse 1 μm silica particles (1000 ppm) from Geltech (Orlando) in pH 6.1 phosphate buffer, with an ionic strength of 0.005M was flowed at a wall shear rate of 21 s$^{-1}$ over each nanoparticle-containing silica flat. (The flow chamber was oriented vertically so that gravity did not affect particle adhesion.) The silica particle capture rates represent steady-state particle capture, typically established within 1 min of microparticle flow. The rates were measured well before surface crowding of the silica microparticles hindered the capture of additional microparticles. As would be understood by those in the art, the data are representative of single microparticle-collector contacts.

The preceding examples and discussion illustrate how surfaces presenting nanoparticles capture and hold silica microparticles flowing in solution at controlled pH and ionic strength. Referring to the non-limiting embodiments demonstrated, without the cationic nanoparticles, the silica surfaces repel the 1 μm silica spheres; however, the nanoparticles produce localized attractions that trap flowing micron-scale particles. The rate of microparticle capture increases linearly with the surface density of cationic nanoparticles, starting at the origin, indicating that each nanoparticle is capable of capturing and holding a microparticle. When the Debye length is smaller than the nanoparticle height on the surface, micro-particles resist hydrodynamic shear forces exceeding 9 pN; however, as the Debye length is increased towards the nanoparticle size (and protrusion from the surface) the silica microparticles release in gentle flow. This represents a crossover from dominance by localized attractions at low ionic strength to control by the background electrostatic repulsive field. Thus the electrostatic forces dominate hydrodynamic and van der Waals forces, such that particles can be captured and released by changing ionic conditions. This behavior could be employed in extremely sensitive detector elements. Also, because the localized nature of single nanoparticle-microparticle contacts differs from the many contacts that occur between most cells as part of signaling, using single nanoparticles may prove a useful means to manipulate cells and bacteria without triggering biological response.

We claim:

1. A method of selective particle separation, said method comprising: providing a heterogeneous surface comprising a surface member and a plurality of components coupled thereto and extending therefrom, said components spaced about said surface member and having a density thereon, said surface heterogeneity providing different interactions of said surface member and said spaced components with a particle exposed thereto; exposing a particle mixture to said heterogeneous surface; and separating particles from said mixture with said heterogeneous surface, said separation selective for a said particle.

2. The method of claim 1 wherein said particles are dimensioned from about 30 nm to about 20 μm.

3. The method of claim 1 wherein said heterogeneity comprises at least one of different electrostatic interactions and van der Waals interactions with said particle.

4. The method of claim 3 wherein each of said surface member and said components has a net charge at least partially sufficient for selective particle separation.

5. The method of claim 3 wherein said components have a surface charge density at least partially sufficient for selective particle separation.

6. The method of claim 1 wherein each said component comprises a cross-sectional dimension up to about 50 nm, said dimension providing component extension beyond said surface member.

7. The method of claim 6 wherein said components comprise an average spatial density, said spatial density at least partially sufficient for selective particle separation from said mixture.

8. The method of claim 7 wherein at least one of rate of particle adhesion and strength of particle adhesion varies with spatial density.

9. The method of claim 6 wherein a said component comprises a nanoparticulate composition comprising a metal core and a shell thereabout, said component cross-sectional dimension comprising said core/shell diameter.

10. The method of claim 9 wherein said core comprises a precious metal, and said shell comprises ligands selected from cationic and anionic ligands.

11. The method of claim 10 wherein said nanoparticulate composition comprises cationic ligands, said component comprising a net positive charge, and said surface member comprises a net negative charge.

12. The method of claim 1 wherein said particles are collected from said surface, for exposure to another particle mixture.

13. The method of claim 1, wherein the plurality of components extends by a distance of at least a length of a repulsive background field of the surface.

14. The method of claim 13, wherein the length of the repulsive background field of the surface is a Debye length.

* * * * *